(12) United States Patent
Rosch et al.

(10) Patent No.: US 7,626,700 B2
(45) Date of Patent: Dec. 1, 2009

(54) MOSAIC QUANTIFICATION BY BIREFRINGENCE MEASUREMENT

(75) Inventors: William Rogers Rosch, Corning, NY (US); Horst Schreiber, Rochester, NY (US)

(73) Assignee: Corning Incorporated, Corning, NY (US)

( * ) Notice: Subject to any disclaimer, the term of this patent is extended or adjusted under 35 U.S.C. 154(b) by 442 days.

(21) Appl. No.: 11/591,810

(22) Filed: Nov. 2, 2006

(65) Prior Publication Data

US 2008/0123077 A1 May 29, 2008

(51) Int. Cl.
*G01J 4/00* (2006.01)
(52) U.S. Cl. .................... 356/365; 356/30; 356/432
(58) Field of Classification Search ............. 356/30–31, 356/432–435, 365
See application file for complete search history.

(56) References Cited

U.S. PATENT DOCUMENTS 4,133,309 A * 1/1979 Kohler et al. .......... 128/205.27

6,782,075 B2 * 8/2004 Pell .............................. 378/73

OTHER PUBLICATIONS

B. C. Cullity *Elements of X-Ray Diffraction* Addison-Wesley Series In Metallurgy and Materials. pp. 100-101.

* cited by examiner

*Primary Examiner*—Gregory J Toatley, Jr.
*Assistant Examiner*—Iyabo S Alli
(74) *Attorney, Agent, or Firm*—Walter M. Douglas

(57) ABSTRACT

A crystal optical material is illuminated at a wavelength of light that does not ionize the crystal optical material. Birefringence is measured between a plurality of voxels within the crystal optical material having spatial dimensions small enough to distinguish optical propagations of the light encountering boundary regions between subgrains of the crystal mosaic from optical propagations of the light through the subgrains themselves. The measured birefringence is evaluated for quantifying a characteristic of the crystal matrix. Metrics describing the crystal matrix are associated with performance of the crystal optical material.

28 Claims, 2 Drawing Sheets

MOSAIC QUANTIFICATION BY BIREFRINGENCE MEASUREMENT

FIELD OF THE INVENTION

The invention relates to the measurement of crystal structures and, in particular, to the quantification of crystal mosaics by birefringence measurements.

BACKGROUND OF THE INVENTION

Some crystal materials can perform well as optical materials, particularly for transmitting shorter wavelengths of light such as ultraviolet or deep ultraviolet light where most amorphous optical materials are less transmissive or more susceptible to optical damage. However, the ordered structure of crystalline optical materials in the form of repeating cells of atoms or molecules arranged in lattice can have directionally dependent properties unlike amorphous materials like glass. For example, refractive index can be affected by the direction at which light encounters periodic crystal structures. Such directionally dependent refractive index properties are referred to as birefringence.

Uniaxial crystal materials, such as calcium fluoride, which express three-dimensional symmetry on a unit cell scale, exhibit little birefringence except at shorter wavelengths in the deep ultraviolet spectrum where sub-unit asymmetries are apparent on a finer scale. Such birefringence, to the extent the birefringence remains consistent throughout the crystal structures, can be accommodated or even exploited by optical designs.

In actual crystals, defects interrupt the periodic order of crystal structures, which can degrade the performance of crystal optical materials. A major defect that affects the long-range cell order is a grain boundary. This is the junction or intersection of two crystals of the same material that have different orientations. The discontinuity in crystal structure is apparent when crossing a grain boundary and is generally not tolerable in precision optical materials. Such grain boundaries can be plentiful or rare depending on the crystal's content or history.

Another recurring defect in crystal structure is a subgrain boundary. As the name implies, these boundaries form inside individual crystal grains. Subgrain boundaries generally comprise groupings of dislocations or line defects in the material. Dislocations can be thought of as imperfect packing of the crystal unit cells. In the region immediately surrounding the dislocation, the dislocation causes disorder in the crystal structure but does not generally affect the material order further away from the dislocation site.

Dislocations can move through a grain of a crystal as the crystal material is stressed. Dislocations that group together into a network form the subgrain boundaries. These networks are energetically favorable to form because they decrease the energy associated with disorder from each individual dislocation. When crossing a subgrain boundary, a very slight orientation change occurs, which is much smaller than when crossing a grain boundary. The material on either side of a subgrain boundary will have almost the same orientation.

When subgrains are apparent throughout a crystal material, the crystal material is described as having a mosaic structure, made up by many smaller individual tiles (i.e., subgrains) that are all slightly misaligned relative to each other. In optical materials, high levels of mosaic are undesirable and thought to shorten the lifetime (e.g., service life) of crystal optical materials, particularly with respect to the transmission of shorter wavelengths in the deep ultraviolet spectrum.

Several methods are known for assessing the mosaic layout of crystal materials. However, each has drawbacks associated with measurement time, measurement equipment, material damage, or a lack of quantifiable results.

Since mosaic is disorder of the crystal lattice (i.e., relative misalignments within the periodic crystal structure), techniques that can determine lattice orientations are capable of detecting mosaic. X-ray probes are most widely used for determining relative orientations of the crystal lattice. For example, X-ray diffraction, soft X-rays, or X-ray topography are all capable of providing information on the mosaic level of a crystal.

X-ray diffraction uses a relatively low-powered, white source (low temporal coherence) X-ray beam to determine crystal lattice orientations. X-rays directed to the crystal surface constructively interfere with the crystal structure when the X-ray energy and lattice spacings and angles meet specific criteria. For example, constructive interference occurs at particular diffraction angles (referred to as Bragg diffraction) when the optical path-length difference between rays scattered from adjacent lattice planes equal an integral number of wavelengths. By collecting and analyzing the diffracted X-rays, the orientation of the crystal structure can be determined. In addition, by determining the crystal lattice orientations at several different locations in the crystal sample, an indication of the amount of mosaic present in the crystal sample can be estimated. However, such multiple exposures can take hours to complete per sample, and the X-rays expose the crystal to ionizing radiation that can damage the crystal material of the sample.

Soft X-rays are a much faster method of measuring mosaic. A much higher intensity X-ray beam passes directly though the crystal. Similar to X-ray diffraction, when certain conditions are met in the structure, some of the beam is deflected. By capturing this deflected beam and determining its width, a measure of mosaic can be estimated. The width of the deflected beam is affected by the amount of disorder in the crystal sample, and the beam is narrowest when the mosaic level is lowest. Scanning the soft X-ray beam allows for spatial information to be collected throughout the crystal sample. However, specialized equipment is required to carry out this method, which is available in only a few locations in the world. In addition, the X-rays expose the crystal sample to damaging ionizing radiation.

X-ray topography is another X-ray technique that can estimate the mosaic level. A high intensity X-ray beam (from a synchrotron) is highly collimated by passing the beam through slits that can be 100 meters apart. The highly collimated beam is directed to the crystal sample and a diffraction spot is collected. The crystal sample is translated through the beam to map reflections from its surface. Because the beam is so collimated, the diffraction spot can then be enlarged to see an image of how the crystal structure of the crystal surface varies. Again, highly specialized equipment is needed, and the exposure of the crystal sample to ionizing radiation can cause damage.

Besides the X-ray techniques for mosaic identification, several other methods have been used to estimate the amount of mosaic in crystal samples. The simplest involves cleaving the crystal sample and visually inspecting its surface. Since subgrains cause only slight changes in the crystal orientation, the material can be cleaved. Inspection of the cleaved surface of a crystal with high mosaic reveals a large number of sub-regions that are all slightly misaligned. However, the inspection is limited to the cleaved surface of the sample, the cleaving itself causes obvious damage, and the estimate of mosaic is highly subjective. At best a relative rating of low, medium, or high can be given.

Another method commonly used is to inspect crystal mosaic uses a cross polarizer to see the effects of stress on the crystal sample. Stress causes birefringence, and a cross polarizer shows areas with higher levels of stress as different colors. Mosaic, since it is disorder of the lattice, makes this color shift less uniform. Mosaic images from the cross polarizer appear as cobweb structures or as clouds. The method allows a quick mosaic evaluation, but is highly subjective and can only yield relative ratings of low, medium, and high. Even these ratings can be questionable, since the amount of birefringence seen is affected by both the crystal orientation and the tested sample length. A sample material with very low stress has low amounts of stress birefringence and therefore a low signal output, which makes estimates of mosaic more difficult.

Two other methods for observing mosaic effects involve using a shadowgraph technique or an optical homogeneity measurement. Because of disorder in the crystal sample, light passing through the sample can be slightly deflected. This can be seen using a high-powered light source projected through the crystal sample onto a special screen. Quantification, however, is problematic. Optical homogeneity of a sample crystal can also be measured as an indication of mosaic. However, the method tends to be labor intensive and quite slow.

SUMMARY OF INVENTION

The invention involves a new approach to mosaic quantification, which is intended to overcome certain of the drawbacks of the prior art by preserving crystal sample integrity, providing timely measurement results, and avoiding the need for specialized equipment with limited availability. In one or more preferred embodiments, a high spatially resolved birefringence measurement is made having a spatial resolution fine enough to resolve the stress created at the sub-grain boundaries. The birefringence measurements can be made using optically transmissive wavelengths. Because the birefringence is measured at such a fine scale and with optically transmissive wavelengths, mosaic level can be quantified to high accuracy without inflicting damage to the crystal sample.

New metrics can be defined to link the birefringence measurements to mosaic levels or more directly to the expected consequences of the corresponding mosaic levels. For example, the birefringence variations associated with the mosaic can be statistically described and equated by empirically derived relationships to the performance or service life of the crystal sample. The statistical quantification of the mosaic within undisturbed crystal samples allows the same samples to be further evaluated in association with their intended use. The further associations can be used to assess material quality for such purposes as qualifying optical components or driving material improvements relating to the level or other characteristics of the mosaic.

One version of the invention can be practiced as a method of estimating service life of a crystal optical material having a lattice mosaic of imperfectly aligned subgrains. Birefringence within the crystal optical material is measured at a spatial resolution that discerns discontinuities between the subgrains within the mosaic. The birefringence variations among the measurements are characterized according to a metric, and the metric is applied as an estimate of a service life of the crystal optical material.

Preferably, the crystal optical material is irradiated with light and the light is collected from voxels within the crystal optical material having spatial dimensions less than the discontinuities between the mosaic subgrains. The irradiating light preferably has a wavelength within a transmission spectrum of the crystal optical material.

The crystal optical material can be relatively moved and successively irradiated over different spatial regions of the crystal optical material for measuring birefringence characteristics of the voxels within the plurality of different spatial regions of the crystal optical material. The birefringence characteristics can be quantified as a statistical measure of birefringence variation among the measured voxels. For example, the statistical measure of birefringence variation can be used to quantify a prevalence of the discontinuities between the subgrains over a region of measurement or to quantify magnitudes of the discontinuities between the subgrains over a region of measurement.

The metrics quantifying statistical variations can be related to the service life of the crystal optical material based on a correlation between the characterization of the birefringence variation and a measure of the service life of the crystal optical material. For example, the service life can be measured as an accrued dose of radiation transmitted through the crystal optical material at which a predetermined reduction in performance is reached.

Another version of the invention can be practiced as a method of quantifying a crystal mosaic as a measure of material quality. A crystal optical material is illuminated at a wavelength of light that does not ionize the crystal optical material. Light is collected from a plurality of voxels within the crystal optical material having spatial dimensions small enough to distinguish optical propagations of the light encountering boundary regions between subgrains of the crystal mosaic from optical propagations of the light through the subgrains themselves. The birefringence exhibited by the plurality of voxels is measured, and birefringence variations among the voxels are evaluated for quantifying a characteristic of the crystal matrix.

The birefringence variations can be evaluated for discerning a prevalence of the subgrain boundaries over a region of measurement or for discerning a degree of disorder at the subgrain boundaries over a region of measurement. The crystal optical material is preferably illuminated with polarized light. In collecting the light from the plurality of voxels within the crystal optical material, a region of the crystal optical material is preferably imaged onto a detector array. Successive images from a plurality of regions of the crystal optical material can be collected for quantifying the crystal matrix throughout a larger portion of the crystal optical material. The voxels are preferably resolved to a planar spatial resolution of less than 50 microns, and more preferably at a spatial resolution of less than 10 microns.

Another version of the invention can be practiced as a method of predicting the performance of crystal optical samples. Birefringence within a plurality of the crystal optical samples is measured at a resolution that discerns discontinuities between subgrains within the crystal optical samples. Birefringence variations within the crystal optical samples are characterized in accordance with a metric. A performance characteristic of the crystal optical samples is also measured, and values of the metric are correlated with the measured performance characteristics of the crystal optical samples for predicting the performance of other crystal optical samples having similar metric values.

The birefringence variations within the crystal optical samples can be characterized in accordance with a plurality of different metrics, and values of the plurality of different metrics can be correlated with the measured performance characteristics of the crystal optical samples. Preferably, one of the metrics having a higher correlation than other of the metrics is used for predicting the performance of the other crystal optical samples.

The metric can be a statistical measure of birefringence variations within the crystal optical samples. The metric can also be arranged to evaluate a density of subgrain boundaries within the crystal optical samples. The performance characteristic of the crystal optical samples can be related to the service lives of the crystal optical samples. The service life of the crystal optical sample can be related to an accrued dose of radiation transmitted through the crystal optical samples at which a predetermined reduction in performance is reached.

BRIEF DESCRIPTION OF THE DRAWING FIGURES

DETAILED DESCRIPTION OF THE INVENTION

Figure 1:
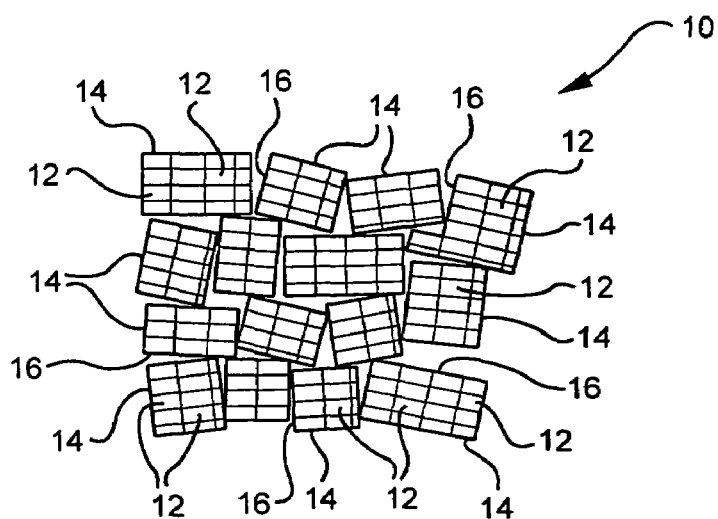
FIG. 1 is a schematic illustration of the mosaic structure of a single crystal grain in which groups of unit cells are organized into subgrains that are misaligned with respect to one another.

In a schematic representation of a mosaic structure of a single crystal grain 10 as shown in FIG. 1, dislocations between some of the unit cells 12 divide the crystal grain 10 into an assembly of subgrains 14 that slightly misalign groups of unit cells 12 with respect to one another. The misalignments shown in FIG. 1 are greatly exaggerated to distinguish boundaries 16 where the dislocations occur from regions within the subgrains 14 where the periodic crystal order among the unit cells 12 is maintained. The misaligned subgrains 14 resemble the tiles of a mosaic, and the arrangement of the subgrains 14 and particularly the network of their boundaries 16 are referred to as mosaic.

As a measure of local defects in the crystal structure, a high level of mosaic is generally undesirable for optically transmissive materials. For example, a relationship has been found between mosaic level and lifetime issues (e.g., the service life) of optical crystal samples as well as other issues including transmissivity and dispersion. Thus, mosaic can be quantified as a metric for predicting lifetime or assessing other performance issues of crystal optical materials.

With fine enough spatial resolution, birefringence measurements can be used to measure the stress at the subgrain boundaries at which dislocations are collected from the more regular order of the subgrains themselves. A spatial resolution of less than 50 microns can be used to detect the mosaic patterns of calcium fluoride and similar crystal optical materials, however, spatial resolutions of less than 10 microns are preferred for resolving additional details.

Figure 2A:
FIGS. 2A-2C are depictions of three levels of mosaic within a calcium fluoride sample ranging from low to high as apparent from contrast coded birefringence measurements.
Figure 2B:
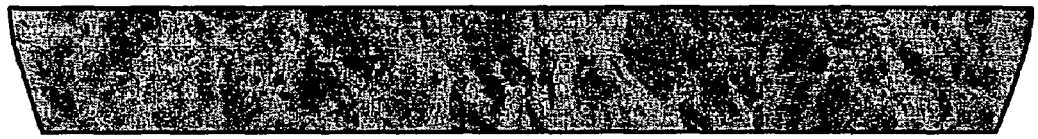
Figure 2C:
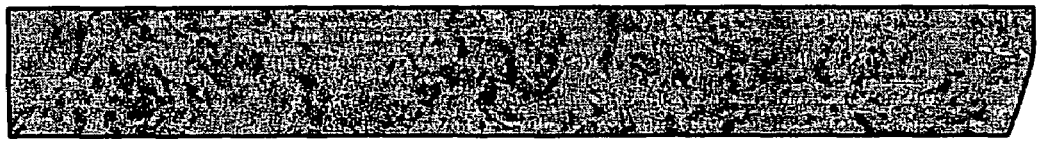

FIGS. 2A through 2C depict low, medium, and high levels of mosaic (e.g., concentrations) of mosaic in a calcium fluoride crystal as apparent from gray-scale coded birefringence measurements. Concentrations of dislocations along subgrain boundaries are apparent as lighter gray areas against a darker gray background of the regular periodic crystal structure. Visual inspection of the scaled birefringence measurements can generally distinguish different overall levels of mosaic, but further statistical qualification is needed to establish objective metrics that can more finely distinguish the performance-related effects of mosaic.

Figure 3:
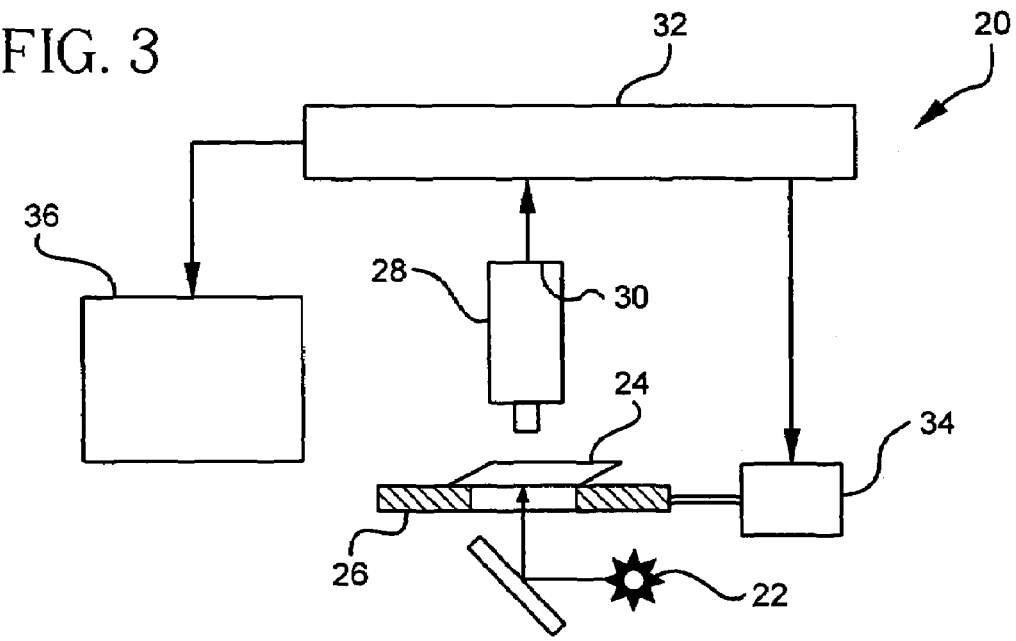
FIG. 3 is a depiction of apparatus for finely measuring birefringence patterns within a crystal optical sample.

A birefringence measuring system 20 is depicted in FIG. 3. A light source 22, such as a lamp or laser, illuminates a crystal optical sample 24 through a stage 26 on which the crystal optical sample 24 is mounted. A polarization controlled imaging device 28 images light from crystal optical sample 24 onto a detector array 30 for detecting polarization retardance as well as the associated orientation of the major polarization axes, which are systematic of the birefringence exhibited by the crystal optical sample 24. The imaging device 28 provides for gathering light within individual voxels (i.e., spatial volumes) of the crystal optical sample 24 and for directing the light from the individual voxels onto individual detectors, also referred to as pixels, within the detector array 30. A voxel is defined as a three-dimensional pixel (VOlume piXEL) that represents a quantity of three-dimensional data just as a pixel represents a point or a cluster of points in two-dimensional data. It is a term commonly used in scientific and medical systems that process three-dimensional images.

A processor 32 collects information from the detector array 30 for quantifying local birefringence values as well as for quantifying global birefringence variations throughout the measured region for characterizing the mosaic properties of the crystal optical sample 24. A driver 34 also connected to the processor 32 translates the stage 26 through a range of additional positions for measuring birefringence variations within other regions of the crystal optical sample 24. Conventional stitching algorithms can be used to assemble data from multiple measurements into a common data map that can be processed for quantifying the global birefringence variations of a larger volume of the crystal optical sample 24. Images captured or otherwise processed by the processor 32 can be displayed on a monitor 36 along with graphical, tabular, and other numerical or pictorial data presentations derivable from the retardance measurements.

A commercially available quantitative birefringence imaging system capable of use in accordance with the invention is available from CRI, Inc. of Woburn, Mass. under the trade name LC-Polscope IM. The LC-Polscope system incorporates a microscope objective together with polarization controls for resolving low-level birefringence in crystal samples as a resolution of less than 10 microns. The light source 22, which can operate within the visible spectrum, produces light capable of transmitting through the crystal optical sample 24 without damaging the crystal optical sample 24.

Figure 4:
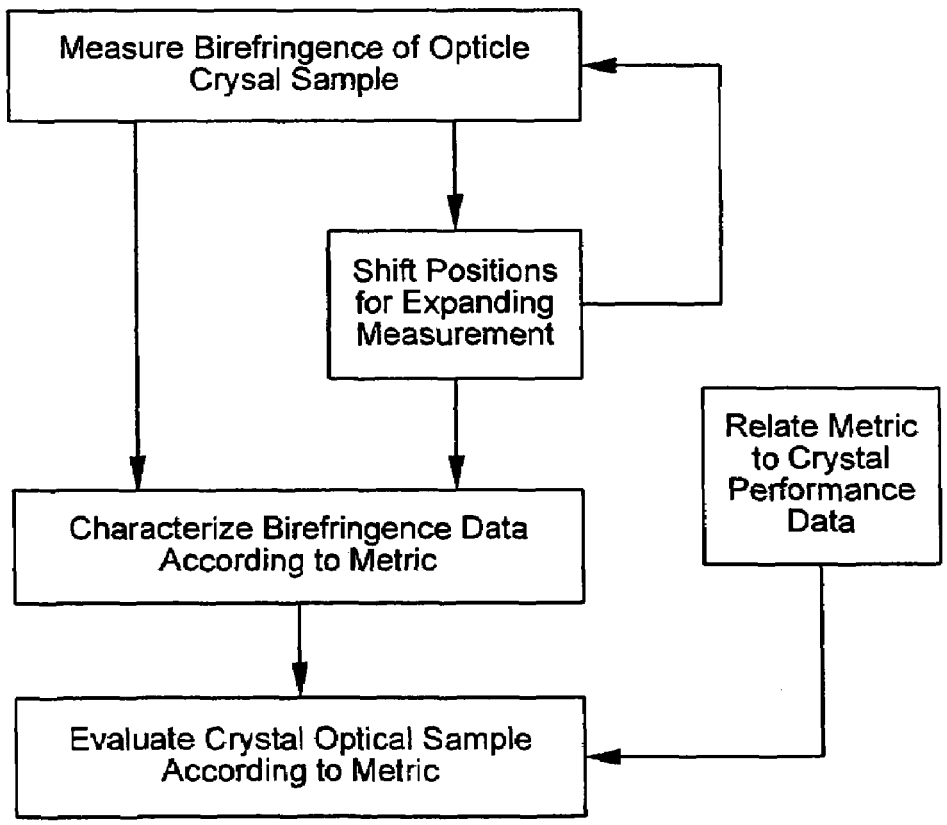
FIG. 4 is a flow chart showing a method of evaluating the mosaic structure of a crystal optical material based on measurements of birefringence.

Presented in FIG. 4 is a flow chart by which birefringence characteristics of a crystal optical sample are processed as a way of characterizing the mosaic structure of the crystal optical material for the further purpose of quantifying or qualifying the expected performance of the crystal optical sample. The birefringence measurements can be taken at a single relative position between the imaging device 28 and the crystal optical sample 24 or at a succession of relatively shifted positions by which more of the crystal optical sample 24 can be measured.

Although the birefringence data can be collectively processed to produce an average value, such as a mean, the statistical variations among the data are believed to be more descriptive of the mosaic structure responsible for performance variations including differences in the service lives of crystal optical materials. Examples of such statistical variation include the (a) standard deviation of the birefringence measurements, (b) descriptors of the range or histogram shape of the birefringence values, (c) descriptors of the local slopes involving the rate or frequency with which the birefringence values change over distance, (d) "RTM" descriptors of average peak to valley measurement, (e) "RZ" descriptors of average distance between a given number (e.g., five) of highest peaks and valleys within an evaluation length, (f) "S" descriptors of the mean spacing between local peaks over the evaluation length, and (g) "RMS" descriptors of statistical departures from a null value.

Empirical performance data, including data relating to service life, can be collected for the measured samples of different crystal optical materials for identifying correlations between the mosaic structure as statistically described and the measured performance of the same materials. Once so correlated, particular metrics can be defined to quantify or qualify new crystal optical samples, such as for qualifying crystal optical parts for use, for monitoring changes in the crystal optical materials accompanying their use, or for driving improvements in the manufacture of new crystal optical parts. Changes in the mosaic in response to applied stress can also be measured.

Although the invention has been described with respect to particular embodiments, those of skill in the art will appreciate the many variations that can be made within the overall teaching of this invention relating to quantifying crystal matrices.

The invention claimed is:

1. A method of estimating service life of a crystal optical material having a lattice mosaic of imperfectly aligned subgrains comprising steps of:
    measuring birefringence within the crystal optical material at a spatial resolution discerning discontinuities between subgrains within the mosaic,
    characterizing birefringence variations among the measurements according to a metric, and
    applying the metric as an estimate of a service life of the crystal optical material.

2. The method of claim 1 in which the step of measuring includes the substeps of irradiating the crystal optical material with light and collecting the light from voxels within the crystal optical material having spatial dimensions less than the discontinuities between the mosaic subgrains.

3. The method of claim 2 in which the step of irradiating the crystal optical material includes irradiating the crystal optical material with light having a wavelength within a transmission spectrum of the crystal optical material.

4. The method of claim 2 in which the step of measuring includes successively irradiating and collecting light from the voxels over different spatial regions of the crystal optical material for measuring birefringence characteristics of the voxels within the plurality of different spatial regions of the crystal optical material.

5. The method of claim 4 in which the step of characterizing the birefringence variations among the measurements includes evaluating the birefringence measurements of the voxels across the plurality of different spatial regions of the crystal optical material.

6. The method of claim 1 in which the step of characterizing includes quantifying the mosaic as a statistical measure of birefringence variation among the measured voxels.

7. The method of claim 6 in which the statistical measure of birefringence variation quantifies a prevalence of the discontinuities between the subgrains over a region of measurement.

8. The method of claim 6 in which the statistical measure of birefringence variation quantifies magnitudes of the discontinuities between the subgrains over a region of measurement.

9. The method of claim 1 in which the step of applying the metric includes estimating the service life of the crystal optical material based on a correlation between the characterization of the birefringence variation and a measure of the service life of the crystal optical material.

10. The method of claim 9 in which the service life is measured as an accrued dose of radiation transmitted through the crystal optical material at which a predetermined reduction in performance is reached.

11. A method of quantifying a crystal mosaic as a measure of material quality comprising steps of:
    illuminating a crystal optical material at a wavelength of light that does not ionize the crystal optical material,
    collecting the light from a plurality of voxels within the crystal optical material having spatial dimensions small enough to distinguish optical propagations of the light encountering boundary regions between subgrains of the crystal mosaic from optical propagations of the light through the subgrains themselves,
    measuring the birefringence exhibited by the plurality of voxels, and
    evaluating birefringence variations among the plurality of voxels for quantifying a characteristic of the crystal matrix.

12. The method of claim 11 in which the step of evaluating includes evaluating the birefringence variations for discerning a prevalence of the subgrain boundaries over a region of measurement.

13. The method of claim 11 in which the step of evaluating includes evaluating the birefringence variations for discerning a degree of disorder at the subgrain boundaries over a region of measurement.

14. The method of claim 11 in which the step of illuminating includes illuminating the crystal optical material with deep ultraviolet light having a wavelength less than 200 nanometers.

15. The method of claim 11 in which the step of illuminating includes illuminating the crystal optical material with polarized light.

16. The method of claim 11 in which the step of collecting the light from the plurality of voxels within the crystal optical material includes imaging a region of the crystal optical material onto a detector array.

17. The method of claim 16 in which the step of collecting the light from the plurality of voxels includes successively imaging a plurality of regions of the crystal optical material onto the detector array.

18. The method of claim 16 in which the voxels are resolved to a planar spatial resolution of less than 50 microns.

19. The method of claim 16 in which the voxels are resolved to a planar spatial resolution of less than 10 microns.

20. The method of claim 11 in which the steps of illuminating and collecting are repeated for a plurality of different spatial regions of the crystal optical material, and the step of measuring includes measuring the birefringence exhibited by the plurality of voxels across the different spatial regions.

21. A method of predicting performance of a crystal optical samples comprising steps of
    measuring birefringence within a plurality of the crystal optical samples at a resolution that discerns discontinuities between subgrains within the crystal optical samples,
    characterizing birefringence variations within the crystal optical samples in accordance with a metric,
    measuring a performance characteristic of the crystal optical samples, and correlating values of the metric with the measured performance characteristics of the crystal optical samples for predicting the performance of other crystal optical samples having similar metric values.

22. The method of claim 21 in which the step of characterizing include characterizing birefringence variations within the crystal optical samples in accordance with a plurality of different metrics.

23. The method of claim 22 in which the step of correlating values of the metric includes correlating values of the plurality of different metrics with the measured performance characteristics of the crystal optical samples.

24. The method of claim 23 in which one of the metrics having a higher correlation than other of the plurality of metrics is used for predicting the performance of the other crystal optical samples.

25. The method of claim 21 in which the metric is a statistical measure of birefringence variations within the crystal optical samples.

26. The method of claim 21 in which the metric evaluates a density of subgrain boundaries within the crystal optical samples.

27. The method of claim 21 in which the performance characteristic is related to the service lives of the crystal optical samples.

28. The method of claim 27 in which the service life of the crystal optical sample is related to an accrued dose of radiation transmitted through the crystal optical samples at which a predetermined reduction in performance is reached.

* * * * *